US008798952B2

(12) United States Patent
Govari et al.

(10) Patent No.: US 8,798,952 B2
(45) Date of Patent: *Aug. 5, 2014

(54) WEIGHT-BASED CALIBRATION SYSTEM FOR A PRESSURE SENSITIVE CATHETER

(75) Inventors: Assaf Govari, Haifa (IL); Andres Claudio Altmann, Haifa (IL); Yaron Ephrath, Karkur (IL)

(73) Assignee: Biosense Webster (Israel) Ltd. (IL)

( * ) Notice: Subject to any disclaimer, the term of this patent is extended or adjusted under 35 U.S.C. 154(b) by 159 days.

This patent is subject to a terminal disclaimer.

(21) Appl. No.: 12/797,693

(22) Filed: Jun. 10, 2010

(65) Prior Publication Data

US 2011/0307207 A1    Dec. 15, 2011

(51) Int. Cl.
A61B 5/103    (2006.01)
A61M 25/00    (2006.01)
G01L 1/04    (2006.01)

(52) U.S. Cl.
USPC .......................................... 702/101; 702/98

(58) Field of Classification Search
USPC ................................................. 702/98, 101
See application file for complete search history.

(56) References Cited

U.S. PATENT DOCUMENTS

| 3,841,150 | A |   | 10/1974 | Pearson |
| 3,971,364 | A |   | 7/1976 | Fletcher et al. |
| 4,764,114 | A | * | 8/1988 | Jeffcoat et al. ............... 433/72 |
| 4,856,993 | A |   | 8/1989 | Maness et al. |
| 4,930,494 | A |   | 6/1990 | Takehana et al. |
| 5,263,493 | A |   | 11/1993 | Avitall |
| 5,368,564 | A |   | 11/1994 | Savage |
| 5,391,199 | A |   | 2/1995 | Ben-Haim |
| 5,462,527 | A |   | 10/1995 | Stevens-Wright et al. |
| 5,487,757 | A |   | 1/1996 | Truckai et al. |
| 5,499,542 | A |   | 3/1996 | Morlan |
| 5,542,434 | A |   | 8/1996 | Imran et al. |
| 5,558,091 | A |   | 9/1996 | Acker et al. |
| 5,563,354 | A |   | 10/1996 | Kropp |
| 5,662,124 | A |   | 9/1997 | Wilk |

(Continued)

FOREIGN PATENT DOCUMENTS

DE    19750441 A    6/1999
EP    928601 A1    7/1999

(Continued)

OTHER PUBLICATIONS

Instron Marketing Brochure, "Medical Device Testing Systems", Instron 2007 http://web.archive.org/web/20080318092822/http://www.instron.com.tr/wa/library/StreamFile.aspx?doc=1678&download=true.*

(Continued)

Primary Examiner — Jonathan C Teixeira Moffat
Assistant Examiner — Regis Betsch (57) ABSTRACT

A calibration apparatus includes a fixture, which is coupled to hold a distal end of a medical probe. A plurality of weights, which have respective masses and respective bottom surfaces that are oriented at respective angles with respect to the distal end of the probe, are coupled to rest on a distal tip of the probe so as to apply to the distal tip respective force vectors that cause a deformation of the distal tip relative to the distal end. A calibration processor is configured to receive from the probe measurements indicative of the deformation of the distal tip in response to the force vectors, and to compute, based on the measurements, the masses and the angles, calibration coefficients for assessing the force vectors as a function of the measurements.

12 Claims, 3 Drawing Sheets

(56) References Cited

U.S. PATENT DOCUMENTS

| | | | |
|---|---|---|---|
| 5,673,695 A | 10/1997 | McGee et al. |
| 5,680,860 A | 10/1997 | Imran |
| 5,685,878 A | 11/1997 | Falwell et al. |
| 5,728,149 A | 3/1998 | Laske et al. |
| 5,769,843 A | 6/1998 | Abela et al. |
| 5,826,576 A | 10/1998 | West |
| 5,833,608 A | 11/1998 | Acker |
| 5,836,894 A | 11/1998 | Sarvazyan |
| 5,860,974 A | 1/1999 | Abele |
| 5,861,024 A | 1/1999 | Rashidi |
| 5,902,248 A | 5/1999 | Millar et al. |
| 5,916,147 A | 6/1999 | Boury |
| 5,944,022 A | 8/1999 | Nardella et al. |
| 5,947,320 A | 9/1999 | Bordner et al. |
| 5,964,757 A | 10/1999 | Ponzi |
| 5,974,320 A | 10/1999 | Ward et al. |
| 5,983,126 A | 11/1999 | Wittkampf |
| 6,048,329 A | 4/2000 | Thompson et al. |
| 6,063,022 A | 5/2000 | Ben-Haim |
| 6,123,699 A | 9/2000 | Webster, Jr. |
| 6,171,277 B1 | 1/2001 | Ponzi |
| 6,177,792 B1 | 1/2001 | Govari et al. |
| 6,183,463 B1 | 2/2001 | Webster, Jr. |
| 6,198,974 B1 | 3/2001 | Webster, Jr. |
| 6,201,387 B1 | 3/2001 | Govari |
| 6,203,493 B1 | 3/2001 | Ben-Haim |
| 6,216,027 B1 | 4/2001 | Willis et al. |
| 6,226,542 B1 | 5/2001 | Reisfeld |
| 6,239,724 B1 | 5/2001 | Doron et al. |
| 6,241,724 B1 | 6/2001 | Fleischman et al. |
| 6,266,551 B1 | 7/2001 | Osadchy et al. |
| 6,272,371 B1 | 8/2001 | Shlomo |
| 6,272,672 B1 | 8/2001 | Conway |
| 6,301,496 B1 | 10/2001 | Reisfeld |
| 6,332,089 B1 | 12/2001 | Acker et al. |
| 6,334,837 B1 | 1/2002 | Hein |
| 6,335,617 B1 | 1/2002 | Osadchy et al. |
| 6,351,549 B1 | 2/2002 | Souluer |
| 6,436,059 B1 | 8/2002 | Zanelli |
| 6,456,864 B1 | 9/2002 | Swanson et al. |
| 6,484,118 B1 | 11/2002 | Govari |
| 6,551,302 B1 | 4/2003 | Rosinko et al. |
| 6,569,098 B2 | 5/2003 | Kawchuk |
| 6,574,492 B1 | 6/2003 | Ben-Haim et al. |
| 6,584,856 B1 | 7/2003 | Biter et al. |
| 6,602,242 B1 | 8/2003 | Fung et al. |
| 6,612,992 B1 | 9/2003 | Hossack et al. |
| 6,618,612 B1 | 9/2003 | Acker et al. |
| 6,690,963 B2 | 2/2004 | Ben-Haim et al. |
| 6,695,808 B2 | 2/2004 | Tom |
| 6,711,429 B1 | 3/2004 | Gilboa et al. |
| 6,727,371 B2 | 4/2004 | Muller et al. |
| 6,814,733 B2 | 11/2004 | Schwartz et al. |
| 6,835,173 B2 | 12/2004 | Couvillon, Jr. |
| 6,892,091 B1 | 5/2005 | Ben-Haim et al. |
| 6,915,149 B2 | 7/2005 | Ben-Haim |
| 6,945,956 B2 | 9/2005 | Waldhauser et al. |
| 6,964,205 B2 | 11/2005 | Papakostas et al. |
| 6,973,339 B2 | 12/2005 | Govari |
| 6,997,924 B2 | 2/2006 | Schwartz et al. |
| 7,077,823 B2 | 7/2006 | McDaniel |
| 7,156,816 B2 | 1/2007 | Schwartz et al. |
| 7,235,070 B2 | 6/2007 | Vanney |
| 7,297,116 B2 | 11/2007 | Varghese et al. |
| 7,306,593 B2 | 12/2007 | Keidar et al. |
| 7,306,599 B2 | 12/2007 | Karasawa et al. |
| 7,311,704 B2 | 12/2007 | Paul et al. |
| 7,397,364 B2 | 7/2008 | Govari |
| 7,435,232 B2 | 10/2008 | Liebschner |
| 7,465,288 B2 | 12/2008 | Dudney et al. |
| 7,481,774 B2 | 1/2009 | Brockway et al. |
| 7,536,218 B2 | 5/2009 | Govari et al. |
| 7,604,605 B2 | 10/2009 | Zvuloni |
| 7,662,151 B2 | 2/2010 | Crompton, Jr. et al. |
| 7,681,432 B2 | 3/2010 | Hay et al. |
| 7,686,767 B2 | 3/2010 | Maschke |
| 7,914,440 B2 | 3/2011 | Otawara |
| 7,959,601 B2 | 6/2011 | McDaniel et al. |
| 7,984,659 B2 | 7/2011 | Fujimoto et al. |
| 8,043,216 B2 | 10/2011 | Matsumura |
| 8,046,049 B2 | 10/2011 | Govari et al. |
| 8,083,691 B2 | 12/2011 | Goldenberg et al. |
| 8,137,275 B2 | 3/2012 | Fan et al. |
| 8,374,819 B2 * | 2/2013 | Govari et al. ............ 702/104 |
| 2001/0047129 A1 | 11/2001 | Hall et al. |
| 2001/0047133 A1 | 11/2001 | Gilboa et al. |
| 2002/0002329 A1 | 1/2002 | Avitall |
| 2002/0065455 A1 | 5/2002 | Ben-Haim et al. |
| 2002/0068866 A1 | 6/2002 | Zikorus et al. |
| 2002/0068931 A1 | 6/2002 | Wong et al. |
| 2002/0165461 A1 | 11/2002 | Hayzelden et al. |
| 2002/0193781 A1 | 12/2002 | Loeb |
| 2003/0120150 A1 | 6/2003 | Govari |
| 2003/0120195 A1 | 6/2003 | Milo et al. |
| 2003/0130615 A1 | 7/2003 | Tom |
| 2003/0158494 A1 | 8/2003 | Dahl et al. |
| 2003/0187389 A1 | 10/2003 | Morency et al. |
| 2004/0049255 A1 | 3/2004 | Jain et al. |
| 2004/0064024 A1 | 4/2004 | Sommer |
| 2004/0068178 A1 | 4/2004 | Govari |
| 2004/0097806 A1 | 5/2004 | Hunter et al. |
| 2004/0102769 A1 | 5/2004 | Schwartz et al. |
| 2004/0147920 A1 | 7/2004 | Keidar |
| 2004/0244464 A1 | 12/2004 | Hajdukiewicz et al. |
| 2004/0254458 A1 | 12/2004 | Govari |
| 2005/0033135 A1 | 2/2005 | Govari |
| 2005/0080429 A1 | 4/2005 | Freyman et al. |
| 2005/0096590 A1 | 5/2005 | Gullickson et al. |
| 2005/0228274 A1 | 10/2005 | Boese et al. |
| 2005/0277875 A1 | 12/2005 | Selkee |
| 2006/0009690 A1 | 1/2006 | Fuimaono et al. |
| 2006/0009735 A1 | 1/2006 | Viswanathan et al. |
| 2006/0015096 A1 | 1/2006 | Hauck et al. |
| 2006/0064038 A1 | 3/2006 | Omata et al. |
| 2006/0074297 A1 | 4/2006 | Viswanathan |
| 2006/0173480 A1 | 8/2006 | Zhang |
| 2006/0184106 A1 | 8/2006 | McDaniel et al. |
| 2006/0200049 A1 | 9/2006 | Leo et al. |
| 2006/0247618 A1 | 11/2006 | Kaplan et al. |
| 2007/0021742 A1 | 1/2007 | Viswanathan |
| 2007/0060832 A1 | 3/2007 | Levin |
| 2007/0060847 A1 * | 3/2007 | Leo et al. ............ 600/587 |
| 2007/0100332 A1 | 5/2007 | Paul et al. |
| 2007/0106114 A1 | 5/2007 | Sugimoto et al. |
| 2007/0106165 A1 | 5/2007 | Tulkki |
| 2007/0142749 A1 | 6/2007 | Khatib et al. |
| 2007/0151391 A1 * | 7/2007 | Larkin et al. ............ 74/490.06 |
| 2007/0156114 A1 | 7/2007 | Worley et al. |
| 2007/0161882 A1 | 7/2007 | Pappone |
| 2007/0167740 A1 | 7/2007 | Grunewald et al. |
| 2007/0167818 A1 | 7/2007 | Osborn et al. |
| 2007/0167819 A1 | 7/2007 | Osborn et al. |
| 2007/0179492 A1 | 8/2007 | Pappone |
| 2007/0185397 A1 | 8/2007 | Govari et al. |
| 2007/0191829 A1 | 8/2007 | McGee et al. |
| 2007/0197939 A1 | 8/2007 | Wallace et al. |
| 2007/0233044 A1 | 10/2007 | Wallace et al. |
| 2007/0282211 A1 | 12/2007 | Ofek et al. |
| 2008/0009750 A1 | 1/2008 | Aeby et al. |
| 2008/0015568 A1 | 1/2008 | Paul et al. |
| 2008/0051704 A1 | 2/2008 | Patel et al. |
| 2008/0065111 A1 * | 3/2008 | Blumenkranz et al. ...... 606/130 |
| 2008/0071267 A1 | 3/2008 | Wang et al. |
| 2008/0077049 A1 | 3/2008 | Hirshman |
| 2008/0146918 A1 | 6/2008 | Magnin et al. |
| 2008/0183075 A1 | 7/2008 | Govari et al. |
| 2008/0200843 A1 | 8/2008 | Williams et al. |
| 2008/0249467 A1 | 10/2008 | Burnett et al. |
| 2008/0249522 A1 | 10/2008 | Pappone et al. |
| 2008/0255540 A1 | 10/2008 | Selkee |
| 2008/0269606 A1 | 10/2008 | Matsumura |
| 2008/0275428 A1 | 11/2008 | Tegg et al. |
| 2008/0275442 A1 | 11/2008 | Paul et al. |
| 2008/0275465 A1 | 11/2008 | Paul et al. |

(56) References Cited

U.S. PATENT DOCUMENTS

| | | |
|---|---|---|
| 2008/0281319 A1 | 11/2008 | Paul et al. |
| 2008/0287777 A1 | 11/2008 | Li et al. |
| 2008/0288038 A1 | 11/2008 | Paul et al. |
| 2008/0294144 A1 | 11/2008 | Leo et al. |
| 2008/0294158 A1 | 11/2008 | Pappone et al. |
| 2009/0010021 A1 | 1/2009 | Smith et al. |
| 2009/0093806 A1 | 4/2009 | Govari et al. |
| 2009/0138007 A1 | 5/2009 | Govari et al. |
| 2009/0158511 A1 | 6/2009 | Maze et al. |
| 2009/0177111 A1 | 7/2009 | Miller et al. |
| 2009/0275966 A1 | 11/2009 | Mitusina |
| 2009/0287118 A1 | 11/2009 | Malek |
| 2009/0294361 A1 | 12/2009 | Larsen |
| 2009/0306515 A1 | 12/2009 | Matsumura et al. |
| 2009/0306650 A1 | 12/2009 | Govari et al. |
| 2010/0063478 A1 | 3/2010 | Selkee |
| 2010/0069921 A1 | 3/2010 | Miller et al. |
| 2010/0121138 A1 | 5/2010 | Goldenberg et al. |
| 2010/0137845 A1 | 6/2010 | Ramstein et al. |
| 2010/0152574 A1 | 6/2010 | Erdman et al. |
| 2010/0160770 A1 | 6/2010 | Govari et al. |
| 2010/0160778 A1 | 6/2010 | Eskandari et al. |
| 2010/0168620 A1 | 7/2010 | Klimovitch et al. |
| 2010/0168918 A1 | 7/2010 | Zhao et al. |
| 2010/0292566 A1 | 11/2010 | Nagano et al. |
| 2010/0298826 A1 | 11/2010 | Leo et al. |
| 2011/0054354 A1 | 3/2011 | Hunter et al. |
| 2011/0054355 A1 | 3/2011 | Hunter et al. |
| 2011/0071436 A1 | 3/2011 | Althoefer et al. |
| 2011/0130648 A1 | 6/2011 | Beeckler et al. |
| 2011/0153252 A1 | 6/2011 | Govari et al. |
| 2011/0153253 A1* | 6/2011 | Govari et al. .................. 702/98 |
| 2011/0160556 A1 | 6/2011 | Govari |
| 2011/0172538 A1 | 7/2011 | Sumi |
| 2011/0184406 A1 | 7/2011 | Selkee |
| 2011/0307207 A1 | 12/2011 | Govari et al. |
| 2012/0004576 A1 | 1/2012 | Govari et al. |
| 2012/0041295 A1 | 2/2012 | Schultz |
| 2012/0089358 A1 | 4/2012 | Ludwin et al. |
| 2012/0108988 A1 | 5/2012 | Ludwin et al. |
| 2012/0149966 A1 | 6/2012 | Ludwin et al. |
| 2012/0149967 A1 | 6/2012 | Ludwin et al. |
| 2012/0150075 A1 | 6/2012 | Ludwin et al. |
| 2012/0184864 A1 | 7/2012 | Harlev et al. |
| 2012/0184865 A1 | 7/2012 | Harlev et al. |
| 2012/0253167 A1 | 10/2012 | Bonyak et al. |
| 2012/0259194 A1 | 10/2012 | Selkee |
| 2012/0271145 A1 | 10/2012 | Govari et al. |
| 2012/0310116 A1 | 12/2012 | Ludwin et al. |
| 2012/0316407 A1 | 12/2012 | Anthony et al. |
| 2013/0018306 A1 | 1/2013 | Ludwin |
| 2013/0096551 A1 | 4/2013 | Govari et al. |
| 2013/0131489 A1 | 5/2013 | Govari et al. |
| 2013/0131663 A1 | 5/2013 | Govari et al. |
| 2013/0172875 A1 | 7/2013 | Govari et al. |

FOREIGN PATENT DOCUMENTS

| | | |
|---|---|---|
| EP | 980693 A1 | 2/2000 |
| EP | 1502555 A1 | 2/2005 |
| EP | 1586281 A1 | 10/2005 |
| EP | 1690564 A1 | 8/2006 |
| EP | 1743575 A2 | 1/2007 |
| EP | 1820464 A1 | 8/2007 |
| EP | 1897581 A2 | 3/2008 |
| EP | 2000789 A2 | 12/2008 |
| EP | 2 047 797 A2 | 4/2009 |
| EP | 2127604 A1 | 12/2009 |
| EP | 2130508 B1 | 12/2009 |
| EP | 2196143 A1 | 6/2010 |
| EP | 2305115 A1 | 4/2011 |
| EP | 2338412 A1 | 6/2011 |
| EP | 2172240 B1 | 12/2012 |
| EP | 2338411 B1 | 11/2013 |
| JP | 8243168 A | 9/1996 |
| JP | 2000126301 A | 5/2000 |
| JP | 2005040215 | 2/2005 |
| JP | 2005/345215 A | 12/2005 |
| JP | 2006064465 A | 3/2006 |
| WO | WO 95/10326 A | 4/1995 |
| WO | WO 96/05768 | 2/1996 |
| WO | WO 97/29678 A | 8/1997 |
| WO | WO 97/29709 A | 8/1997 |
| WO | WO 97/29710 A | 8/1997 |
| WO | WO 98/29032 A | 7/1998 |
| WO | WO 03/020139 A | 3/2003 |
| WO | WO 2006/086152 A | 8/2006 |
| WO | WO 2006/092563 A | 9/2006 |
| WO | WO 2006/135483 A2 | 12/2006 |
| WO | WO 2007/015139 A2 | 2/2007 |
| WO | WO 2007/025230 A | 3/2007 |
| WO | WO 2007/050960 A | 5/2007 |
| WO | WO 2007/067938 A | 6/2007 |
| WO | WO 2007/076312 A2 | 7/2007 |
| WO | WO 2007/082216 A | 7/2007 |
| WO | WO 2007/098494 A1 | 8/2007 |
| WO | WO 2007/111182 A | 10/2007 |
| WO | WO 2008/053402 A1 | 5/2008 |
| WO | WO 2008/147599 A1 | 12/2008 |
| WO | WO 2009/065140 A1 | 5/2009 |
| WO | WO 2009/078280 A | 6/2009 |
| WO | WO 2009/085470 A | 7/2009 |
| WO | WO 2009/147399 A | 12/2009 |
| WO | WO 2010/008975 A | 1/2010 |
| WO | WO 2011/046874 A1 | 4/2011 |

OTHER PUBLICATIONS

Instron, "Series 3300 Load Frames, Reference Manual Equipment", Instron pp. 1-5 and 1-10, 2004.*

J. Peirs et al., "Design of an Optical Force Sensor for Force Feedback during Minimally INvasive Robotic Surgery", Eurosensors XVII, 2003 http://www.mech.kuleuven.be/micro/pub/medic/Paper_Eurosensors_2003_MIS_sensor_extended.pdf.*

EP Search Report No: EP 11 16 9251 dated Sep. 15, 2011.

U.S. Appl. No. 13/971,955, filed Aug. 21, 2013.

U.S. Appl. No. 13/975,778, filed Aug. 26, 2013.

U.S. Appl. No. 14/021,125, filed Sep. 9, 2013.

Biter, William J. et al., "Magnetic Wire Strain Sensor", 33rd International Sampe Technical Conference, Nov. 5-8, 2001, vol. 33, pp. 12-23, Seattle, WA.

Biter, William J. et al., "Magnetic Wire for Monitoring Strain in Composites", *Sensors*, Jun. 2001, www.sensormag.com, pp. 110-114.

Guo, Shuxiang et al., "Control and Experimental results of a Catheter Operating System", Feb. 21-26, 2009, Proceedings of the 2008 IEEE, International Conference on Robotics and Biomimetics, Bankok, Thailand, pp. 91-95.

Kanagaratnam, Prapa et. al., "Experience of robotic catheter ablation in humans using novel remotely steerable catheter sheath", Journal of Interventional Cardiac Electrophysiology. Volume 21, No. 1, p. 19-26 (2008).

Okumura, M.D. Yasuo et al. "A Systematic Analysis of *In Vivo* Contact Forces on Virtual Catheter Tip/Tissue Surface Contact during Cardiac Mapping and Intervention", Journal of Cardiovascular Electrophysiology, Jun. 2008, pp. 632-640, vol. 19, No. 6.

Partial European Search Report mailed on Sep. 18, 2009 from related European Patent Application No. 08253265.6.

Partial European Search Report mailed on Dec. 7, 2009 from related European Patent Application No. 09251502.2.

European Search Report mailed on Mar. 8, 2010 from related European Patent Application No. 09252143.4.

Partial European Search Report mailed on Mar. 29, 2010 from related European Patent Application No. 09252879.3.

European Search Report mailed on Mar. 2, 2011 from related European Patent Application No. 10175931.4.

European Search Report mailed on Mar. 28, 2011 from related European Patent Application No. 10252189.5.

(56) References Cited

OTHER PUBLICATIONS

European Search Report mailed on Mar. 28, 2011 from related European Patent Application No. 10252191.1.
European Search Report mailed on Mar. 30, 2011 from related European Patent Application No. 10252020.2.
European Search Report mailed on May 16, 2011 from related European Patent Application No. 10252232.3.
European Search Report mailed on Aug. 5, 2011 from related European Patent Application No. 11158804.2.
European Search Report mailed on Sep. 20, 2011 from related European Patent Application No. 11250066.5.
European Search Report mailed on Oct. 28, 2011 from related European Patent Application No. 11171842.5.
European Search Report mailed on Nov. 17, 2011 from related European Patent Application No. 11177600.1.
European Search Report mailed on Feb. 15, 2012 from related European Patent Application No. 11182854.7.
European Search Report mailed on May 2, 2012 from related European Patent Application No. 11189326.9.
European Search Report mailed on Jun. 4, 2012 from related European Patent Application No. 12163784.7.
European Search Report mailed on Jul. 20, 2012 from related European Patent Application No. 12161784.9.
European Search Report mailed on Nov. 20, 2012 from related European Patent Application No. 12176163.9.
European Search Report mailed on Feb. 11, 2013 from related European Patent Application No. 11187525.8.
European Search Report mailed on Apr. 9, 2013 from related European Patent Application No. 13150145.4.

* cited by examiner

WEIGHT-BASED CALIBRATION SYSTEM FOR A PRESSURE SENSITIVE CATHETER

FIELD OF THE INVENTION

The present invention relates generally to invasive probes, and specifically to calibrating pressure sensors in invasive probes.

BACKGROUND OF THE INVENTION

A wide range of medical procedures involve placing objects, such as sensors, tubes, catheters, dispensing devices and implants, within the body. Position sensing systems have been developed for tracking such objects. Magnetic position sensing is one of the methods known in the art. In magnetic position sensing, magnetic field generators are typically placed at known positions external to the patient. A magnetic field sensor within the distal end of a probe generates electrical signals in response to these magnetic fields, which are processed in order to determine the position coordinates of the distal end of the probe. These methods and systems are described in U.S. Pat. Nos. 5,391,199, 6,690,963, 6,484,118, 6,239,724, 6,618,612 and 6,332,089, in PCT International Publication WO 1996/005768, and in U.S. Patent Application Publications 2002/0065455 A1, 2003/0120150 A1 and 2004/0068178 A1, whose disclosures are all incorporated herein by reference.

When placing a probe within the body, it may be desirable to have the distal tip of the probe in direct contact with body tissue. The contact can be verified, for example, by measuring the contact pressure between the distal tip and the body tissue. U.S. Patent Application Publications 2007/0100332 and 2009/0093806, whose disclosures are incorporated herein by reference, describe methods of sensing contact pressure between the distal tip of a catheter and tissue in a body cavity using a force sensor embedded in the catheter. The distal tip of the catheter is coupled to the distal end of the catheter insertion tube by a resilient member, such as a spring, which deforms in response to force exerted on the distal tip when it presses against endocardial tissue. A magnetic position sensor within the catheter senses the deflection (location and orientation) of the distal tip relative to the distal end of the insertion tube. Movement of the distal tip relative to the insertion tube is indicative of deformation of the resilient member, and thus gives an indication of the pressure.

SUMMARY OF THE INVENTION

An embodiment of the present invention that is described herein provides a calibration apparatus, including:

a fixture, which is coupled to hold a distal end of a medical probe;

a plurality of weights, having respective masses and respective bottom surfaces that are oriented at respective angles with respect to the distal end of the probe, which are coupled to rest on a distal tip of the probe so as to apply to the distal tip respective force vectors that cause a deformation of the distal tip relative to the distal end; and a calibration processor, which is configured to receive from the probe measurements indicative of the deformation of the distal tip in response to the force vectors, and to compute, based on the measurements, the masses and the angles, calibration coefficients for assessing the force vectors as a function of the measurements.

In some embodiments, the apparatus includes a sensing device coupled to the fixture and configured to measure respective downwards components of the force vectors, and the calibration processor is configured to verify the calibration coefficients responsively to the measured downward components. In an embodiment, the bottom surfaces are coated with a non-stick material. In a disclosed embodiment, the bottom surfaces are coated with a material having a surface texture that matches an inner surface texture of a body organ in which the probe is to operate. In another embodiment, the calibration processor is configured to store the calibration coefficients in a memory that is coupled to the probe. The memory may include an Electronically Erasable Programmable Read Only Memory (E2PROM).

There is additionally provided, in accordance with an embodiment of the present invention, a method for calibration, including:

holding a distal end of a medical probe in a fixture;

lowering onto a distal tip of the probe weights, having respective masses and respective bottom surface that are oriented at respective angles with respect to the distal tip, so as to apply to the distal tip respective force vectors that cause a deformation of the distal tip relative to the distal end;

receiving from the probe measurements indicative of the deformation of the distal tip in response to the force vectors; and computing, based on the measurements, the masses and the angles, calibration coefficients for assessing the force vectors as a function of the measurements.

The present invention will be more fully understood from the following detailed description of the embodiments thereof, taken together with the drawings in which:

DETAILED DESCRIPTION OF EMBODIMENTS

Some invasive probes comprise pressure sensors for measuring the contact pressure between the probe and intra-body tissue. For example, the distal tip of a cardiac catheter may deform in response to the pressure exerted by the distal tip on the endocardial tissue. A position sensor in the catheter measures the deflection of the distal tip, and thus provides an indication of the contact pressure. In many practical cases, however, the relationship between the actual contact pressure and the reading of the position sensor varies from one catheter to another.

In order to ensure accurate pressure measurements, embodiments of the present invention provide methods and systems for calibrating probes (e.g., catheters) fitted with pressure sensors. In some embodiments, a calibration apparatus comprises a fixture (e.g., a base or a jig) for mounting the distal end of the catheter, and multiple weights that can be lowered to rest on the distal tip of the catheter. Each weight 18 has a known mass and a bottom surface that is oriented at a known angle with respect to the distal tip of the catheter. When the weight 18 is lowered so as to press on the distal tip, the weight 18 applies to the distal tip a force vector that depends on its mass and angle. The distal tip deforms in response to this force vector, and the pressure sensor in the catheter produces deformation (i.e., deflection) measurements of its distal tip. A calibration processor accepts the deformation measurements from the catheter and computes, based on the measurements and the known mass and angle, calibration coefficients for assessing the force vector as a function of the deformation measurements at different angles.

In some embodiments, the calibration coefficients are stored as a calibration matrix in a non-volatile memory that is coupled to the catheter. When the catheter is later used in a medical system, the actual pressure exerted by the catheter's distal tip on the body tissue can be derived with high accuracy from the deflection measurements, using the calibration coefficients stored in the matrix. By using weights having different bottom surface angles, the pressure can be estimated from the deformation measurements of the catheter for different angles of incidence between the distal end of the catheter and the body tissue.

In addition to the fixture and weights, in some embodiments the calibration apparatus further comprises a sensing device (e.g., a scale or load cell) coupled to the fixture. When a given weight 18 is lowered on the distal tip of the catheter, the sensing device produces force measurements for verifying the value of the downward component of the force vector applied by the weight 18.

Figure 1:
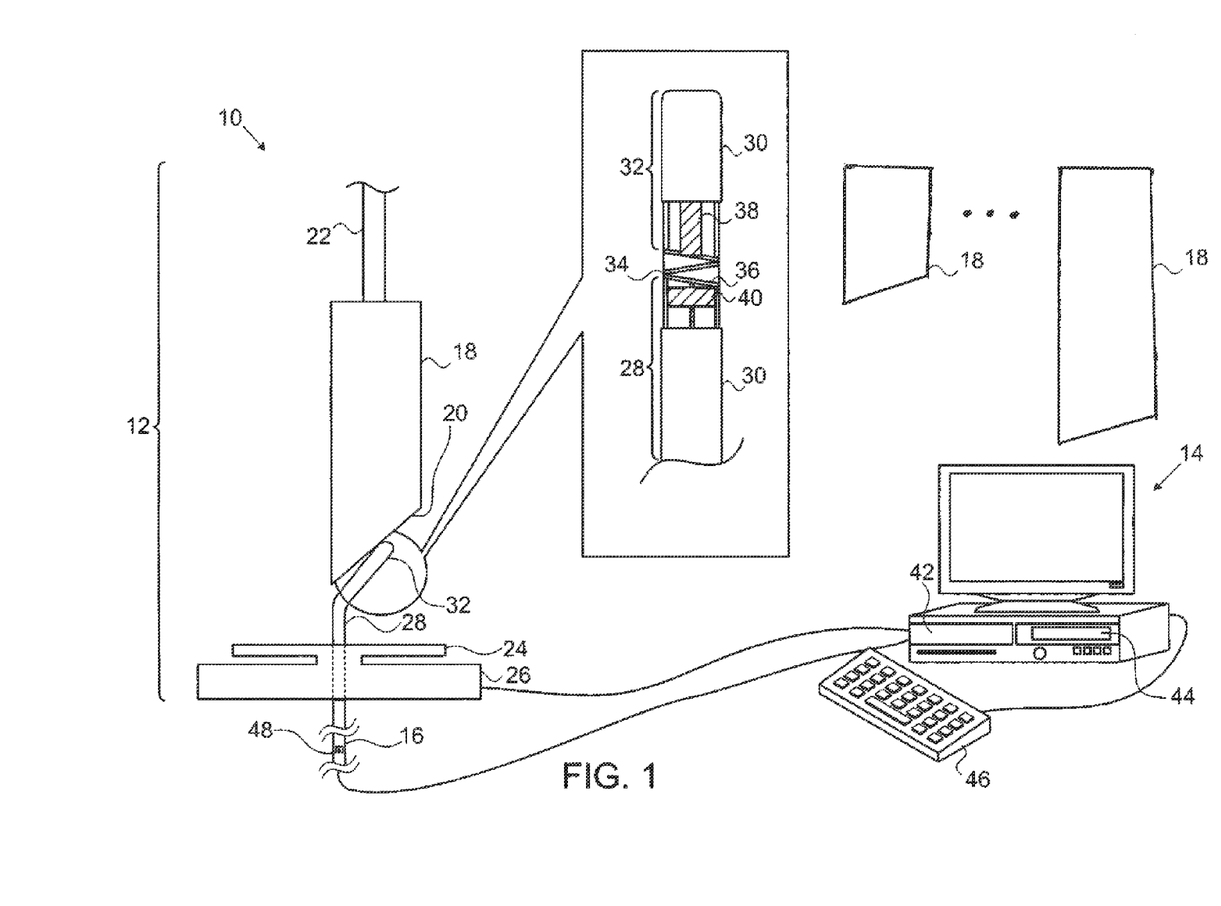
FIG. 1 is a schematic pictorial illustration of a calibration system for a pressure-sensitive catheter, in accordance with an embodiment of the present invention.

FIG. 1 is an illustration of a calibration system 10 for a pressure-sensitive catheter, in accordance with an embodiment of the present invention. System 10 comprises a calibration apparatus 12 coupled to a calibration unit 14. In the embodiment described hereinbelow, system 10 is used for calibrating a probe, in the present example a catheter 16 for therapeutic and/or diagnostic purposes in a heart or in other body organs.

Catheter 16 has a distal end 28, with a distal tip 32 connected to the distal end via a joint 34. Applying sufficient pressure to distal tip 32 (or conversely, if the distal tip applies sufficient pressure against a surface, such as body tissue), catheter 16 will bend at joint 34, thereby deflecting distal tip 32 relative to distal end 28.

Distal end 28 and distal tip 32 of the catheter are both covered by a flexible, insulating material 30. The area of joint 34 is covered, as well, by a flexible, insulating material, which may be the same as material 30 or may be specially adapted to permit unimpeded bending and compression of the joint, (This material is cut away in FIG. 1 in order to expose the internal structure of the catheter.) Distal tip 32 is typically relatively rigid, by comparison with distal end 28.

Distal tip 32 is connected to distal end 28 by a resilient member 36. In FIG. 1, the resilient member has the form of a coil spring, but other types of resilient components may alternatively be used for this purpose. Resilient member 36 permits a limited range of relative movement between tip 32 and distal end 28 in response to forces exerted on the distal tip.

Distal tip 32 contains a magnetic position sensor 38. Sensor 38 may comprise one or more miniature coils, and typically comprises multiple coils oriented along different axes. Distal end 28 comprises a miniature magnetic field generator 40 near resilient member 36. Typically, field generator 40 comprises a coil, which is driven by a current conveyed through the catheter from calibration unit 14.

Alternatively, position sensor 38 may comprise either another type of magnetic sensor, an electrode which serves as a position transducer, or position transducers of other types, such as impedance-based or ultrasonic position sensors. Although FIG. 1 shows a probe with a single position sensor, embodiments of the present invention may utilize probes with more than one position sensor.

The magnetic field created by field generator 40 causes the coils in sensor 38 to generate electrical signals at the drive frequency of the field generator. The amplitudes of these signals will vary depending upon the location and orientation of distal tip 32 relative to distal end 28. A calibration processor 42 in calibration unit 14 processes these signals in order to determine the axial displacement and the magnitude of the angular deflection of the distal tip relative to distal end 28. (Because of the axial symmetry of the field generated by a coil, only the magnitude of the deflection can be detected using a single coil in field generator 40, and not the direction of the deflection. Optionally, field generator 40 may comprise two or more coils, in which case the direction of deflection may be determined, as well). The magnitudes of the displacement and deflection may be combined by vector addition to give a total magnitude of the movement of distal tip 32 relative to distal end 28.

The relative movement of distal tip 32 relative to distal end 28 gives a measure of the deformation of resilient member 36. Thus, the combination of field generator 40 with sensor 38 serves as a pressure sensing system. By virtue of the combined sensing of displacement and deflection, this pressure sensing system reads the pressure correctly regardless of whether the pressure is exerted on distal tip 32 head-on or at an angle. Further details of this sort of probe and position sensor are described in U.S. Patent Application Publications 2009/0093806 and 2009/0138007, cited above.

In some embodiments, catheter 16 also comprises a non-volatile memory 48, such as electronically erasable programmable read only memory ($E^2PROM$) which stores calculation coefficients computed during calibration. As discussed supra, when the catheter is later used in a medical system, the actual pressure exerted by the catheter's distal tip on body tissue can be derived with high accuracy from deflection measurements, using the calibration coefficients stored in memory 48.

Calibration apparatus 12 comprises a fixture 24 such as a base or a jig, configured to hold distal end 28 of catheter 16 upright, and a weight 18 held by a mechanism 22. Weight 18 has an oblique lower surface 20 having a known angle with respect to the distal end of the catheter. The mass of weight 18 is also known. In some embodiments of the present invention, oblique lower surface 20 may be coated with a layer of non-stick material, such as Teflon®, to avoid friction between distal tip 32 and the lower surface, which could cause error in the force calculation. Additionally or alternatively, the oblique lower surface may be coated with a layer whose surface texture matches the inner surface texture of the body organ in which the catheter is to operate (e.g., the texture of the inner surface of a human body cavity wall, such as a heart).

Apparatus 12 may further comprise a sensing device 26 coupled to fixture 24. Sensing device 26 measures the downward mechanical force exerted by catheter 16 on fixture 24. Sensing device 26 may comprise a scale, a load cell or any other suitable device.

Both sensing device 26 and probe 16 are connected to calibration unit 14 via suitable interfaces (e.g., cables and connectors). Calibration unit 14 comprises calibration processor 42, a memory 44, and an input device 46, such as a keyboard. Processor 42 typically comprises a general-purpose computer, with suitable front end and interface circuits for receiving signals from position sensor 38 and sensing device 26, as well as for controlling the other components of calibration unit 14. Processor 42 may be programmed in software to carry out the functions that are described herein. The software may be downloaded to processor 42 in electronic form, over a network, for example, or it may be provided on non-transitory tangible media, such as optical, magnetic or electronic memory media. Alternatively, some or all of the functions of processor may be carried out by dedicated or programmable digital hardware components.

Figure 2:
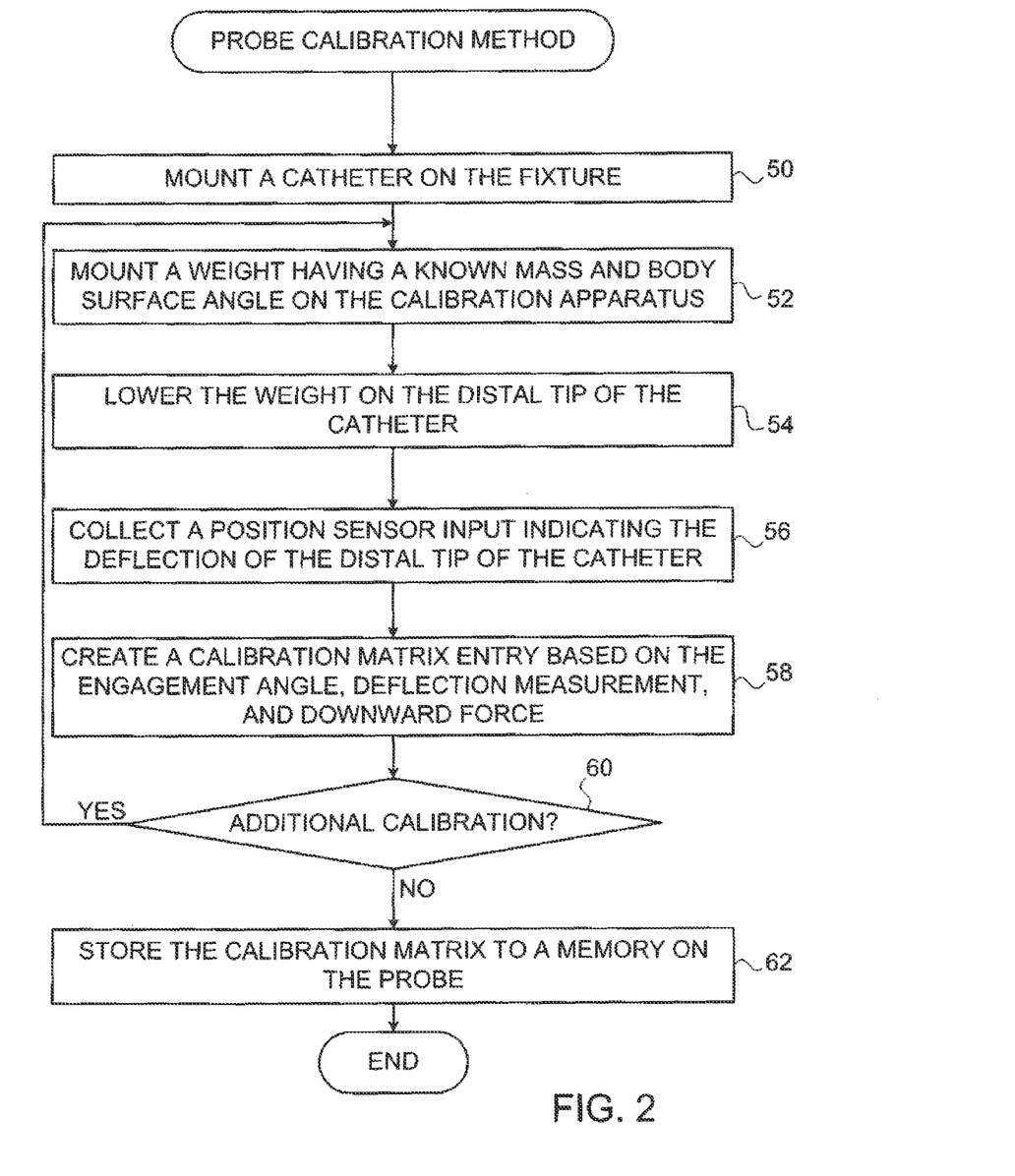
FIG. 2 is a flow diagram that schematically illustrates a method of calibrating a pressure-sensitive catheter, in accordance with an embodiment of the present invention.

FIG. 2 is a flow diagram that schematically illustrates a method of calibrating a pressure-sensitive catheter, in accordance with an embodiment of the present invention. To calibrate catheter 16, the operator mounts the catheter on to fixture 24 (step 50). Weight 18 is mounted on mechanism 22 (step 52) and the mechanism lowers the weigh so that oblique lower surface 20 presses on distal tip 32 (step 54).

Pressing oblique lower surface 20 on distal tip 32 causes the catheter to bend at joint 34, thereby deflecting the distal tip. Position sensor 38 at distal tip 32 outputs a signal indicative of the deflection of the distal tip relative to distal end 28. If apparatus 12 includes a sensing device, then sensing device 26 outputs a signal indicative of the downward mechanical force weight 18 exerts on catheter 16. Both the deflection and downward force measurements are sent to calibration unit 14, where the operator inputs an identification of weight 18 used for this calibration step via keyboard 46. In some embodiments, memory 44 holds, for each weight 18 that can be used in system 10, a numerical index of the weight 18, the mass of the weight 18 and the bottom surface angle of weight 18. The operator enters an index of the currently-used weight 18, thus indicating the mass and angle to processor 42.

Calibration unit 14 accepts the deflection measurements from sensor 38 in the probe (step 56), and processor 42 computes calibration coefficients for calibrating the deflection measurements of probe 16 based on the mass, the engagement angle and the deflection measurement (step 58). By mapping a position measurement from position sensor 38 against the known force vector given by the known mass and angle of the weight 18 (or against the force vector derived from the reading of sensing device 26 and the known angle), the calibration coefficient determines the force on distal tip 32 based on the position sensor measurements. In other words, a given calibration coefficient translates the deflection measurement of tip 32 into an actual pressure reading, for a given engagement angle.

If more calibration points are desired (step 60), then the method returns to step 52 above, where the operator may mount a different weight on mechanism 22. Each weight used during calibration may have a different mass and/or a different oblique lower surface angle. Employing a variety of different weights enables system 10 to test the catheter's tip deflection as a function of the direction and magnitude of the force exerted by each of the weights. Returning to step 60, if no more calibration points are required, processor 42 stores a calibration matrix of the calibration coefficients to memory 48 on the probe (step 62), and the method terminates.

Figure 3:
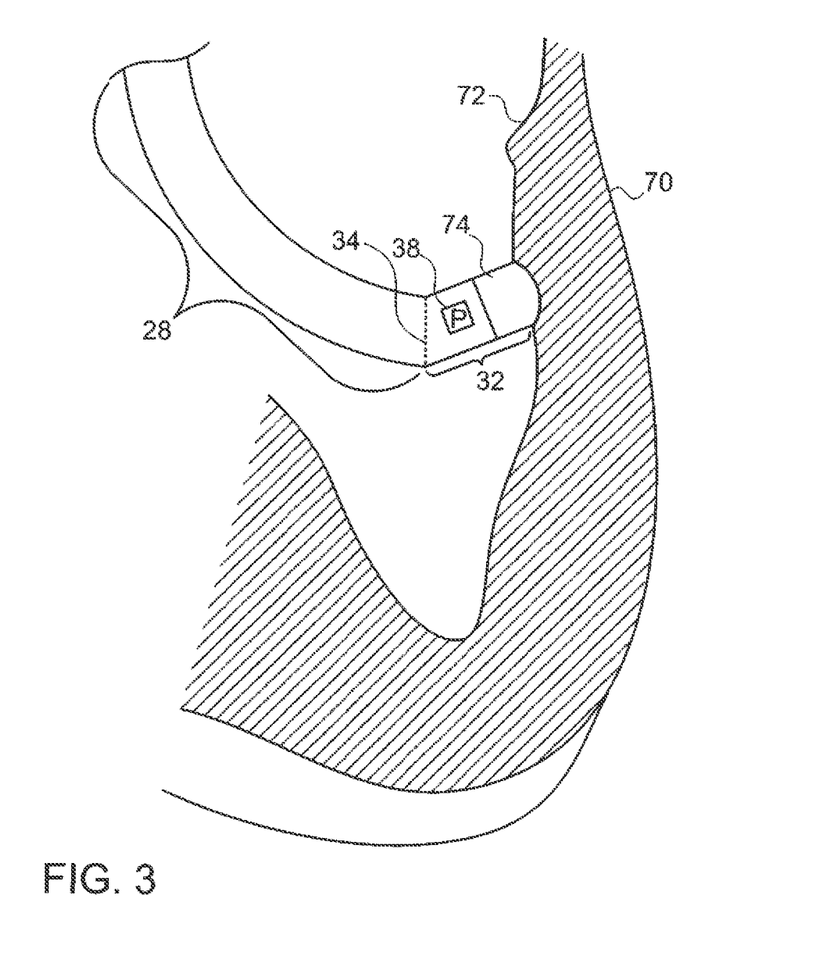
FIG. 3 is a schematic detail view showing the distal tip of a pressure-sensitive catheter in contact with endocardial tissue, in accordance with an embodiment of the present invention.

FIG. 3 is a schematic detail view showing distal tip 32 in contact with an endocardial tissue 72 of a heart 70, in accordance with an embodiment of the present invention. In the present example, tip 32 comprises an electrode 74. In some electrophysiological diagnostic and therapeutic procedures, such as intracardiac electrical mapping, it is important to maintain the proper level of force between electrode 74 and tissue 72. As a medical professional (not shown) presses distal tip 32 against endocardial tissue 72, catheter 16 bends at joint 34. Sufficient force is needed in order to ensure good electrode contact between the distal tip and the tissue. Poor electrical contact can result in inaccurate readings. On the other hand, excessive force can deform the tissue and thus distort the map.

When tip 32 presses against tissue 72, position sensor 38 produces measurements that are indicative of the deflection of tip 32 with respect to distal end 28. The medical imaging system (e.g., mapping system—not shown) translates these measurements into accurate pressure readings using the calibration coefficients (i.e., the calibration matrix) stored in memory 48 of the probe. Thus, calibration of the invasive probe using embodiments of the present invention ensures that the medical professional can accurately control the force exerted by the probe on the tissue.

The corresponding structures, materials, acts, and equivalents of all means or steps plus function elements in the claims below are intended to include any structure, material, or act for performing the function in combination with other claimed elements as specifically claimed. The description of the present disclosure has been presented for purposes of illustration and description, but is not intended to be exhaustive or limiting to the disclosure in the form disclosed. Many modifications and variations will be apparent to those of ordinary skill in the art without departing from the scope and spirit of the disclosure. The embodiment was chosen and described in order to best explain the principles of the disclosure and the practical application, and to enable others of ordinary skill in the art to understand the disclosure for various embodiments with various modifications as are suited to the particular use contemplated.

It is intended that the appended claims cover all such features and advantages of the disclosure that fall within the spirit and scope of the present disclosure. As numerous modifications and changes will readily occur to those skilled in the art, it is intended that the disclosure not be limited to the limited number of embodiments described herein. Accordingly, it will be appreciated that all suitable variations, modifications and equivalents may be resorted to, falling within the spirit and scope of the present disclosure.

What is claimed is:

1. A calibration apparatus, comprising:
    a fixture, which is coupled to hold a distal end of a medical probe;
    a plurality of weights, each having a respective mass and a respective bottom surface that is oriented at a respective angle with respect to the distal end of the probe, each capable of being coupled to rest the entire mass of the weight on a distal tip of the probe so as to apply to the distal tip a respective force vector that causes a deformation of the distal tip relative to the distal end wherein the plurality of weights comprises different masses and different bottom surface angles including oblique bottom surface angles; and
    a calibration processor, which is configured to receive measurements from the probe wherein the measurements are indicative of the deformation of the distal tip in response to the force vectors, and wherein the calibration processor computes a set of calibration coefficients based on the measurements and the respective mass and the respective bottom surface angle for each of the plurality of weights.

2. The apparatus according to claim 1, and comprising a sensing device coupled to the fixture and configured to measure respective downwards components of the force vectors, wherein the calibration processor is configured to verify the calibration coefficients responsively to the measured downward components.

3. The apparatus according to claim 1, wherein the bottom surfaces are coated with a non-stick material.

4. The apparatus according to claim 1, wherein the calibration processor is configured to store the calibration coefficients in a memory that is coupled to the probe.

5. The apparatus according to claim 4, wherein the memory comprises an Electronically Erasable Programmable Read Only Memory ($E^2PROM$).

6. The apparatus of claim 1 wherein the medical probe includes a position sensor that outputs a position measurement indicting a location and an orientation of the distal tip of the medical probe and wherein the calibration processor maps the position measurement from the position sensor with the mass and the bottom surface angle of the weight that causes the distal tip to be in that location and orientation.

7. A method for calibration, comprising:
holding a distal end of a medical probe in a fixture;
lowering onto a distal tip of the probe a plurality of weights one at a time, each having a respective mass and a respective bottom surface that are each oriented at respective angles with respect to the distal tip, so as to apply the entire mass of each weight to the distal tip to generate respective force vectors that cause a deformation of the distal tip relative to the distal end, wherein the plurality of weights comprises different masses and different bottom surface angles including oblique bottom surface angles;
receiving from the probe measurements indicative of the deformation of the distal tip in response to the force vectors; and
computing a set of calibration coefficients based on the probe measurements and the respective mass and the respective bottom surface angle for each of the plurality of weights.

8. The method according to claim 7, and comprising measuring respective downward components of the force vectors using a sensing device coupled to the fixture, and verifying the calibration coefficients responsively to the measured downward components.

9. The method according to claim 7, wherein the bottom surfaces are coated with a non-stick material.

10. The method according to claim 7, and comprising storing the calibration coefficients in a memory coupled to the probe.

11. The method according to claim 10, wherein the memory comprises an Electronically Erasable Programmable Read Only Memory ($E^2PROM$).

12. The method of claim 7 wherein the medical probe includes a position sensor that outputs a position measurement indicating a location and orientation of the distal tip of the medical probe and wherein the computing step maps the position measurement from the position sensor with the mass and the bottom surface angle of the weight that causes the distal to be in that location and orientation.

* * * * *